United States Patent
Monahan et al.

(10) Patent No.: US 7,091,041 B2
(45) Date of Patent: *Aug. 15, 2006

(54) MICELLAR SYSTEMS

(75) Inventors: Sean D. Monahan, Madison, WI (US); Jon A. Wolff, Madison, WI (US); Paul M. Slattum, Madison, WI (US); James E. Hagstrom, Middleton, WI (US); Vladimir G. Budker, Middleton, WI (US)

(73) Assignee: Mirus Bio Corporation, Madison, WI (US)

(*) Notice: Subject to any disclaimer, the term of this patent is extended or adjusted under 35 U.S.C. 154(b) by 0 days.

This patent is subject to a terminal disclaimer.

(21) Appl. No.: 10/627,247

(22) Filed: Jul. 25, 2003

(65) Prior Publication Data

US 2004/0023393 A1 Feb. 5, 2004

Related U.S. Application Data (60) Division of application No. 10/081,461, filed on Feb. 21, 2002, now Pat. No. 6,673,612, which is a continuation-in-part of application No. 09/354,957, filed on Jul. 16, 1999, now Pat. No. 6,429,200.

(51) Int. Cl.
*C12N 15/88* (2006.01)
*A61K 48/00* (2006.01)

(52) U.S. Cl. ............... 435/458; 435/455; 424/450
(58) Field of Classification Search ........... 435/455, 435/458; 424/450

See application file for complete search history.

(56) References Cited

U.S. PATENT DOCUMENTS

| | | | | |
|---|---|---|---|---|
| 5,100,662 | A * | 3/1992 | Bolcsak et al. | 424/450 |
| 6,429,200 | B1 * | 8/2002 | Monahan et al. | 514/44 |
| 6,673,612 | B1 * | 1/2004 | Monahan et al. | 435/458 |
| 6,884,842 | B1 * | 4/2005 | Soane et al. | 525/54.1 |
| 2002/0035082 | A1 * | 3/2002 | Grinstaff et al. | 514/44 |

* cited by examiner

*Primary Examiner*—David Guzo
(74) *Attorney, Agent, or Firm*—Mark K. Johnson; Kirk Ekens (57) ABSTRACT

A complex is described that is deliverable to a cell comprising inserting a nucleic acid or other cargo into a reverse micelle. The reverse micelle has the property to compact the nucleic acid for easier delivery.

10 Claims, 1 Drawing Sheet

FIG. 1

MICELLAR SYSTEMS

This application is a divisional of application Ser. No. 10/081,461; filed Feb. 21, 2002 now U.S. Pat. No. 6,673,612, which is a continuation-in-part of application Ser. No. 09/354,957, filed Jul. 16, 1999, issued as U.S. Pat. No. 6,429,200,

FEDERALLY SPONSORED RESEARCH

N/A

FIELD OF THE INVENTION

The invention generally relates to micellar systems for use in biologic systems. More particularly, a process is provided for the use of reverse micelles for the delivery of nucleic acids and genes to cells.

BACKGROUND

Biologically active compounds such as proteins, enzymes, and nucleic acids have been delivered to the cells using amphipathic compounds that contain both hydrophobic and hydrophilic domains. Typically these amphipathic compounds are organized into vesicular structures such as liposomes, micellar, or inverse micellar structures. Liposomes can contain an aqueous volume that is entirely enclosed by a membrane composed of lipid molecules (usually phospholipids) (R. C. New, p. 1, chapter 1, "Introduction" in Liposomes: A Practical Approach, ed. R. C. New IRL Press at Oxford University Press, Oxford, 1990). Micelles and inverse micelles are microscopic vesicles that contain amphipathic molecules but do not contain an aqueous volume that is entirely enclosed by a membrane. In micelles the hydrophilic part of the amphipathic compound is on the outside (on the surface of the vesicle) whereas in inverse micelles the hydrophobic part of the amphipathic compound is on the outside. The inverse micelles thus contain a polar core that can solubilize both water and macromolecules within the inverse micelle. As the volume of the core aqueous pool increases the aqueous enviromnent begins to match the physical and chemical characteristics of bulk water. The resulting inverse micelle can be referred to as a microemulsion of water in oil (Schelly, Z. A. Current Opinion in Colloid and Interface Science, 37–41, 1997; Castro, M. J. M., Cabral, J. M. S. Biotech. Adv. 6, 151–167, 1988).

Microemulsions are isotropic, thermodynamically stable solutions in which substantial amounts of two immiscible liquids (water and oil) are brought into a single phase due to a surfactant or mixture of surfactants. The spontaneously formed colloidal particles are globular droplets of the minor solvent, surrounded by a monolayer of surfactant molecules. The spontaneous curvature, H0 of the surfactant monolayer at the oil/water interface dictates the phase behavior and microstructure of the vesicle. Hydrophilic surfactants produce oil in water (O/W) microemulsions (H0>0), whereas lipophilic surfactants produce water in oil (W/O) microemulsions. When the hydrophile-lipophile properties of the surfactant monolayer at the water/oil interface are balanced bicontinuous-type microemulsions are formed (H0=0).

Positively-charged, neutral, and negatively-charged liposomes have been used to deliver nucleic acids to cells. For example, plasmid DNA expression in the liver has been achieved via liposomes delivered by tail vein or intraportal routes. Positively-charged micelles have also been used to package nucleic acids into complexes for the delivery of the nucleic acid to cells. Negatively-charged micelles have been used to condense DNA, however they have not been used for the delivery of nucleic acids to cells (Imre, V. E., Luisi, P. L. Biochemical and Biophysical Research Communications, 107, 538–545, 1982). This is because the previous efforts relied upon the positive-charge of the micelles to provide a cross-bridge between the polyanionic nucleic acids and the polyanionic surfaces of the cells. Micelles that are not positively-charged, or that do not form a positively charged complex cannot perform this function. For example, a recent report demonstrated the use of a cationic detergent to compact DNA, resulting in the formation of a stable, negatively-charged particle (Blessing, T., Remy, J. S., Behr, J. P. Proc. Natl. Acad. Sci. USA, 95, 1427–1431, 1998). A cationic detergent containing a free thiol was utilized which allowed for an oxidative dimerization of the surfactant to the disulfide in the presence of DNA. However, as expected, the negatively-charged complex was not effective for transfection. Reverse (water in oil) micelles has also been used to make cell-like compartments for molecular evolution of nucleic acids (Tawfik, D. S. and Griffiths, A. D. Nature Biotechnology 16:652, 1998). Cleavable micellar systems was not used in this system.

In addition, Wolff et al. have developed a method for the preparation of DNA/amphipathic complexes including micelles in which at least one amphipathic compound layer that surrounds a non-aqueous core that contains a polyion such as a nucleic acid (Wolff, J., Budker, V., and Gurevich, V. U.S. Pat. No. 5,635,487).

Cleavable Micelles

A new area in micelle technology involves the use of cleavable surfactants to form the micelle. Surfactants containing an acetal linkage, azo-containing surfactants, elimination of an ammonium salt, quaternary hydrazonium surfactants, 2-alkoxy-N,N-dimethylamine N-oxides, and ester containing surfactants such as ester containing quaternary ammonium compounds and esters containing a sugar have been developed.

These cleavable surfactants within micelles are designed to decompose on exposure to strong acid, ultraviolet light, alkali, and heat. These conditions are very harsh and are not compatible with retention of biologic activity of biologic compounds such as proteins or nucleic acids. Thus, biologically active compounds have not been purified using reverse micelles containing cleavable surfactants.

Complexation of Nucleic Acids with Polycations

Polymers are used for drug delivery for a variety of therapeutic purposes. Polymers have also been used for the delivery of nucleic acids (polynucleotides and oligonucleotides) to cells for therapeutic purposes that have been termed gene therapy or anti-sense therapy. One of the several methods of nucleic acid delivery to the cells is the use of DNA-polycation complexes. It was shown that cationic proteins like histones and protamines or synthetic polymers like polylysine, polyarginine, polyornithine, DEAE dextran, polybrene, and polyethylenimine were effective intracellular delivery agents while small polycations like spermine were ineffective. As a result the main mechanism of DNA translocation to the intracellular space might be non-specific adsorptive endocytosis which may be more effective then liquid endocytosis or receptor-mediated endocytosis. Furthermore, polycations are a very convenient linker for attaching specific receptors to DNA and as result, DNA-polycation complexes can be targeted to specific cell types.

There are a variety of molecules (gene transfer enhancing signals) that can be covalently attached to the gene in order to enable or enhance its cellular transport. These include signals that enhance cellular binding to receptors, cytoplasmic transport to the nucleus and nuclear entry or release from endosomes or other intracellular vesicles.

Nuclear localizing signals enhance the entry of the gene into the nucleus or directs the gene into the proximity of the nucleus. Such nuclear transport signals can be a protein or a peptide such as the SV40 large T ag NLS or the nucleoplasmin NLS.

Other molecules include ligands that bind to cellular receptors on the membrane surface increasing contact of the gene with the cell. These can include targeting group such as agents that target to the asialoglycoprotein receptor by using asiologlycoproteins or galactose residues. Other proteins such as insulin, EGF, or transferrin can be used for targeting. Peptides that include the RGD sequence can be used to target many cells. Chemical groups that react with sulfhydryl or disulfide groups on cells can also be used to target many types of cells. Folate and other vitamins can also be used for targeting. Other targeting groups include molecules that interact with membranes such as fatty acids, cholesterol, dansyl compounds, and amphotericin derivatives.

Size of a DNA complex may be a factor for gene delivery in vivo. Many times, the size of DNA that is of interest is large, and one method of delivery utilizes compaction techniques. The DNA complex needs to cross the endothelial barrier and reach the parenchymal cells of interest. The largest endothelia fenestrae (holes in the endothelial barrier) occur in the liver and have average diameter of 100 nm. The trans-epithelial pores in other organs are much smaller, for example, muscle endothelium can be described as a structure which has a large number of small pores with a radius of 4 nm, and a very low number of large pores with a radius of 20–30 nm.(Rippe, B. Physiological Rev, 1994). The size of the DNA complex is also important for the cellular uptake process. After binding to the target cells the DNA complex should be taken up by endocytosis. Since the endocytic vesicles have a homogenous internal diameter of about 100 nm in hepatocytes, and are of similar size in other cell types, the DNA is compacted to be smaller than 100 nm.

Compaction of DNA

There are two major approaches for compacting DNA:

1. Multivalent cations with a charge of three or higher have been shown to condense DNA. These include spermidine, spermine, $Co(NH3)63+$, $Fe3+$, and natural or synthetic polymers such as histone H1, protamine, polylysine, and polyethylenimine. One analysis has shown DNA condensation to be favored when 90% or more of the charges along the sugar-phosphate backbone are neutralized (Wilson, R. W., Bloomfield, V. A. Biochemistry 18, 2192–2196, 1979).

2. Polymers (neutral or anionic) which can increase repulsion between DNA and its surroundings have been shown to compact DNA. Most significantly, spontaneous DNA self-assembly and aggregation process have been shown to result from the confinement of large amounts of DNA, due to excluded volume effect (Strzelecka, T. E., Rill, R. L. Biopolymers 30, 803–14, 1990; Strzelecka, T. E., Rill, R. L. Biopolymers 30, 57–71, 1990). Since self-assembly is associated with locally or macroscopically crowded DNA solutions, it is expected, that DNA insertion into small water cavities with a size comparable to the DNA will tend to form mono or oligomolecular compact structures.

Micelles and Reverse Micelles

Reverse micelles (water in oil microemulsions) are widely used as a host for biomolecules. Examples exist of both recovery of extracellular proteins from a culture broth and recovery of intracellular proteins. Although widely used, recovery of the biomolecules is difficult due to the stability of the formed micelle and due to incomplete recovery during the extraction process. Similarly, purification of DNA or other biomolecules from endotoxin and plasma is difficult to accomplish. One common method employing Triton results in incomplete separation of the DNA or biomolecules from the emulsion.

Reverse micelles have been widely used as a host for enzymatic reactions to take place. In many examples, enzymatic activity has been shown to increase with micelles, and has allowed enzymatic reactions to be conducted on water insoluble substrates. Additionally, enzymatic activity of whole cells entrapped in reverse micelles has been investigated (Gajjar, L., Singh, A., Dubey, R. S., Srivastava, R. C. Applied Biochemistry and Biotechnology, 66, 159–172, 1997). The cationic surfactant cetyl pyridinuim chloride was utilized to entrap Baker's yeast and Brewer's yeast inside a reverse micelle.

Micelles have also been used as a reaction media. For example, a micelle has been used to study the kinetic and synthetic applications of the dehydrobromination of 2-(p-nitrophenyl) ethyl bromide. Additionally, micelles have found use as an emulsifier for emulsion polymerizations.

Micelles have been utilized for drug delivery. For example, an AB block copolymer has been investigated for the micellar delivery of hydrophobic drugs. Transport and metabolism of thymidine analogues has been investigated via intestinal absorption utilizing a micellar solution of sodium glycocholate. Additionally, several examples of micelle use in transdermal applications have appeared. For example, sucrose laurate has been utilized for topical preparations of cyclosporin A.

SUMMARY

The present invention provides for the transfer of polynucleotides, and biologically active compounds into parenchymal cells within tissues in situ and in vivo, utilizing reverse micelles delivered intravasculary, intrarterially, intravenous, orally, intraduodenaly, via the jejunum (or ileum or colon), rectally, transdermally, subcutaneously, intramuscularly, intraperitoneally, intraparenterally, via direct. injections into tissues such as the liver, lung, heart, muscle, spleen, pancreas, brain (including intraventricular), spinal cord, ganglion, lymph nodes, lymphatic system, adipose tissues, thyroid tissue, adrenal glands, kidneys, prostate, blood cells, bone marrow cells, cancer cells, tumors, eye retina, via the bile duct, or via mucosal membranes such as in the mouth, nose, throat, vagina or rectum or into ducts of the salivary or other exocrine glands.

By "delivered" we mean that the polynucleotide becomes associated with the cell. The polynucleotide can be on the membrane of the cell or inside the cytoplasm, nucleus, or other organelle of the cell. The process of delivering a polynucleotide to a cell has also been commonly termed "transfection" or the process of "transfecting" and also it has been termed "transformation". The polynucleotide could be used to produce a change in a cell that can be therapeutic. The delivery of polynucleotides or genetic material for therapeutic purposes is commonly called "gene therapy". The polynucleotides or genetic material being delivered are generally mixed with transfection reagents prior to delivery.

A biologically active compound is a compound having the potential to react with biological components. Pharmaceuticals, proteins, peptides, hormones, cytokines, antigens and nucleic acids are examples of biologically active compounds. The reverse micelle may be negatively-charged, zwitterionic, or neutral. Additionally, the present invention provides for the purification of biomolecules by solubilizing the biomolecule into a cleavable reverse micelle and then cleaving the micelle under conditions that will not destroy the biological activity of the biomolecule. These processes can be used for transferring nucleic acids or biomolecules into cells or an organism such as for drug delivery, or may also be used for analytical methods.

The process of utilizing cleavable reverse micelles for the purification of biomolecules has advantages over current methodology. Isolation of the biomolecule will be enhanced by cleaving the reverse micelle. This will separate the polar group from the non-polar group on the surfactant and therefore eliminate the formation of emulsions and therefore simplify the isolation process. Cleavage conditions will be such that the biological activity of the biomolecule is not destroyed. Another advantage of the invention is the use of reverse micelles for gene delivery. The reverse micelle can compact the polynucleotide, a critical step for gene delivery, especially in vivo. The micelle containing the compacted polynucleotide can then be utilized as a reaction vesicle in which additional compounds can be added to the DNA. For example, a polycation could be added to the polynucleotide/reverse micelle solution to form a polycation/polynucleotide complex within the reverse micelle. Additionally, the polynucleotide/reverse micelle system is used as a vesicle for template polymerization of the DNA or caging of the DNA in which the polycation is crosslinked. A variety of chemical reactions can take place with in the vesicle preferably without modifying the nucleic acid. The polynucleotide/reverse micelle system also has advantages in that the micelle may be cleaved under physiological conditions involved along the "transfection pathway." The surfactant can be altered so that micellular cleavage occurs at different point along this pathway. By "transfection pathway" we mean any point at which the polynucleotide/reverse micelle system is introduced to a solution (i.e., blood, serum) that contains parenchymal cells, or to the cells (for example the skin or mucousal membranes) through the inclusion of the polynucleotide into the nucleus of the parenchymal cell.

In a preferred embodiment, described is a complex for delivery to a cell, comprising: inserting a nucleic acid into a reverse micelle. A compacting agent may be added to the complex as well as a delivery enhancing ligand or compound.

In a preferred embodiment, a process for delivering a complex to a cell is described, comprising inserting a nucleic acid into a reverse micelle.

In a preferred embodiment, the nucleic acid or biomolecule is solubilized into a reverse micelle with an internal water volume for delivery of the biomolecule to parenchymal cells. A compound can be added to the nucleic acid/micelle mixture. Such compounds include polymers such as polyions (polycations such as spermine, polyamines, polylysine, polyethylimine (PEI), and polyanions), proteins, peptides, enzymes, hydrophobic compounds, and amphipathic compounds (to form a second layer around the micelle). Such compounds include compounds that compact the DNA, provide a cell transfer enhancing ligand or provide another layer to the micelle.

In another preferred embodiment, the nucleic acid or biomolecule is complexed with another molecule prior to micelle formation. For example, a polymer such as polylysine is added to the nucleic acid and then crosslinked to cage the nucleic acid. When a nucleic acid is caged a polymer is formed since the polylysine (or any type of polymer) acts as a monomer that is being included in another polymer.

Another preferred embodiment provides a method of making a compound for delivery to a cell, comprising: adding one or more compounds to the nucleic acid or biomolecule/reverse micelle complex prior to delivery to the cell, thereby providing a deliverable complex. For example, another surfactant or a polyion might be added to the complex. The cell can be a prokaryote or eukaryote and can be a plant, animal or mammalian cell.

Another preferred embodiment provides a method of making a compound for delivery to a cell, comprising: modifying a molecule in the presence of the biomolecule/reverse micelle complex thereby providing a deliverable complex.

In another preferred embodiment, the parenchymal cell is solubilized within a reverse micelle. A reverse micelle containing a polynucleotide would be added to the parenchymal cell containing reverse micelle. After an appropriate amount of time, the parenchymal cell would be purified, and delivered to a mammal.

In another preferred embodiment the biomolecule is solubilized utilizing one of the following procedures.

Procedure 1.
  a) mixing of the biomolecule into an aqueous solution
  b) then mixing the aqueous solution containing the biomolecule with a hydrocarbon or halohydrocarbon containing a surfactant with agitation or sonication Procedure 2.
  Mixing of biomolecule into a solution containing a reverse micelle with agitation or sonication.

Procedure 3.
  a) mixing the biomolecule into an aqueous solution
  b) then extracting the aqueous solution containing the biomolecule with a hydrocarbon or halohydrocarbon containing a reverse micelle and separating the phases.

In another preferred embodiment, the biomolecule is purified comprising a step in which a reverse micelle is destroyed.

In another preferred embodiment, the biomolecule can be purified by utilizing one of the following procedures.

Procedure 1.
  a) mixing of the biomolecule into an aqueous solution
  b) then mixing the aqueous solution containing the biomolecule with a hydrocarbon or halohydrocarbon containing a surfactant with agitation or sonication
  c) cleaving the reverse micelle
  d) extract the biomolecule Procedure 2.
  a) mixing of biomolecule into a solution containing a reverse micelle with agitation or sonication.
  b) cleaving the reverse micelle
  c) extract the biomolecule Procedure 3.
  a) mixing the biomolecule into an aqueous solution
  b) then extracting the aqueous solution containing the biomolecule with a hydrocarbon or halohydrocarbon containing a reverse micelle and separating the phases.
  c) cleaving the reverse micelle
  d) extract the biomolecule In another preferred embodiment, the surfactant is a disulfide of general formula A-S-S-B, which contains a hydrophobic group (A) and a hydrophilic group (B).

In another preferred embodiment, the surfactant can be cleaved in the presence of the nucleic acid or biomolecule under conditions that will not destroy the biological activity of the nucleic acid or biomolecule.

In another preferred embodiment, the surfactant could be chemically modified in the presence of the nucleic acid or biomolecule. For example, the surfactant can be polymerized after micelle formation to form a "shell" or cage around the nucleic acid. The surfactant could be cleaved separating the bulk of its hydrophilic and hydrophobic parts thus destroying its ability to act as a surfactant.

In yet another preferred embodiment, the possible surfactants can be neutral, negatively charged, or zwitterionic but not positively charged. Neutral surfactants include (but not restricted to) polyoxyethylene alcohol's, polyoxyethylene isoalcohol, polyoxyethylene p-t-octyl phenol (Triton), polyoxyethylene nonyiphenol, polyoxyehtylene esters of fatty acids, polyoxyethylene sorbitol esters (Tween) and lipids. Negatively charged surfactants include (but not restricted to) di-(2-ethyl-hexyl) sodium sulfosuccinate (AOT), sodium dodecylsuphate (SDS), sodium dodecylsuphonate, and sodium dodecyl-N-sarcosinate. The zwitterionic surfactant could contain anionic and cationic groups on the alpha and omega positions of a long aliphatic chain. For zwitterionic surfactants that contain both anionic and cationic groups on the alpha and omega positions of a long aliphatic chain, complex formation should be done under acidic conditions so that the surfactant can have a positive charge that will interact with the nucleic acid. The anionic portion is neutralized by being protonated and therefore interacts with the non-aqueous phase. After formation of the complexes, the complexes are extracted into an aqueous solution containing a higher pH than the pH used to form the complexes.

DETAILED DESCRIPTION

A complex is described that is deliverable to a cell comprising inserting a nucleic acid or other cargo into a reverse micelle. The reverse micelle has the property to compact the nucleic acid for easier delivery. The term deliverable means that the complex is capable of being delivered as defined in this specification.

A process for forming a negatively-charged, zwitterionic, or neutral complex for delivery to a cell, comprising forming a cationic reverse micelle using amphipathic molecules. Then inserting a biologically active compound into the cationic reverse micelle.

Subsequently changing the charge of the cationic reverse micelle to a negatively-charged, zwitterionic, or neutral reverse micelle and delivering it to the cell.

The amphipathic molecule may contain a silicon-heteroatom bond. A heteroatom is any atom other than carbon or hydrogen. Examples of a heteroatom include oxygen, nitrogen, phosphorous and sulfer.

A biologically active compound is purified is when it is isolated from a mixture of other compounds. It is purified when its purity is increased where purity is defined as the percentage of the mixture containing the desired biologically active compound. Purification can also indicate a process where the purity of the desired compound is. not increased but the other compounds within the mixture are changed. Purification also indicates the extraction of a biologic compound from one mixture or solution to another mixture or solution. This can include a process where the desired biologically active compound is moved from one solvent to another (also called extraction) or is solubilized within a solvent. A biologically active compound is a compound having the potential to react with biological components for gene therapy purposes. Pharmaceuticals, proteins, peptides, viruses, antigens, carbohydrates (and conjugates), lipids, sacharides, oligonucleotides, and nucleic acids are examples of biologically active compounds.

A surfactant refers to a compound that contains a polar group (hydrophilic) and a non-polar (hydrophobic) group on the same molecule. Cleavable surfactant refers to a surfactant in which the polar group may be separated from the nonpolar group by the removal of a chemical bond located between the two groups, or to a surfactant in which the polar or non-polar group or both may be chemically modified such that the detergent properties of the surfactant are destroyed. Cleavable also means that the surfactant is labile (able to be destroyed or that the detergent properties of the surfactant are able to be destroyed) and that its surfactant properties could be destroyed by other chemical processes than bond cleavage. A disulfide bond that is labile under physiological conditions means the disulfide bond is cleaved more rapidly than oxidized glutathione or any disulfide constructed from thiols in which one of the constituent thiols is more acidic, lower pKa, than glutathione or is activated by intramolecular attack by a free thiol. Constituent in this case means the thiols that are bonded together in the disulfide bond. The surfactant properties of a compound can be destroyed by chemical modification such as converting the polar group into a less polar group. This can be accomplished by a number of chemical modifications including (but not limited to) acylation, alkylation, elimination, reduction or oxidation, of an amine (or its salt), alcohol, diol (di-alcohol) or carboxylic acid groups, or by a multistep process in which several chemical modifications are conducted (for example oxidation of an alcohol to an aldehyde (ketone) followed by nucleophilic addition to the aldehyde (ketone) resulting in an alcohol followed by elimination of the alcohol (or a derivative of it). Reverse (inverse) micelle refers to a surfactant with an internal aqueous pool. By "aqueous" we mean containing water, but can include buffers and salts. Non-aqueous solutions are made up of organic solvents such as hydrocarbon or halohydrocarbon. Buffers are made from a weak acid or weak base and their salts. Buffer solutions resist changes in pH when additional acid or base is added to the solution. Salts are ionic compounds that dissociate into cations and anions when dissolved in solution. Salts increase the ionic strength of a solution, and consequently decrease interactions between nucleic acids with other cations.

A reverse micelle is destroyed when the micelle no longer exists and the monophase no longer exists. A reverse micelle is destroyed when the micelle is disrupted. In a preferred embodiment the reverse micelle is destroyed by chemically modifying the surfactant so that water in oil emulsion is destroyed and the phases separate. A destructible reverse micelle is a reverse micelle that can be destroyed such that the water in oil emulsion is destroyed and the phases separate. A destructible reverse micelle can undergo a biological, chemical, or biochemical reaction such that the reverse micelle is destroyed. Biological, chemical, or biochemical reactions involve the formation or cleavage of ionic and/or covalent bonds. In a preferred embodiment the destructible reverse micelle contains a surfactant that is cleavable, destroyable, or chemically modifiable. The surfactant can be a disulfide of the general formula A-S-S-B, in which chemical group A is a hydrophobic group and chemical group B is a hydrophilic group.

The present invention also relates to a method in which a biologically active compound is delivered to a cell comprising a step in which the biologically active compound is mixed with a biologically-labile surfactant. A biologically-labile surfactant is a surfactant in which the hydrophobic moiety is cleaved from the hydrophilic moiety by cellular processes or its surfactant properties are rendered inactive within the cell, tissue or organism. Examples include surfactants that contain disulfide bonds that are labile within the cell, tissue, or organism.

A transfection reagent is a compound or compounds used in the prior art that bind(s) to or complex(es) with polynucleotides and mediates their entry into cells. The transfection reagent also mediates the binding and internalization of polynucleofides into cells. Examples of transfection reagents include cationic liposomes and lipids, calcium phosphate precipitates, and polylysine complexes. At times, the transfection reagent has a net positive charge that binds to the polynucleotide's negative charge. The transfection reagent mediates binding of polynucleotides to cell via its positive charge (that binds to the cell membrane's negative charge) or via ligands that bind to receptors in the cell. For example, cationic liposomes or polylysine complexes have net positive charges that enable them to bind to DNA.

Other vehicles are also used, in the prior art, to transfer genes into cells. These include complexing the polynucleotides on particles that are then accelerated into the cell. This is termed biolistic or gun techniques. Other methods include eletroporation in which a device is used to give an electric charge to cells. The charge increases the permeability of the cell.

The term "nucleic acid" is a term of art that refers to a polymer containing at least two nucleotides. "Nucleotides" contain a sugar deoxyribose (in DNA) or ribose (in RNA), a base, and a phosphate group. Nucleotides are linked together through the phosphate groups. "Bases" include purines and pyrimidines, which further include natural compounds adenine, thymine, guanine, cytosine, uracil, inosine, and synthetic derivatives of purines and pyrimidines, or natural analogs. Nucleotides are the monomeric units of nucleic acid polymers. A "polynucleotide" is distinguished here from an "oligonucleotide" by containing more than 80 monomeric units; oligonucleotides contain from 2 to 80 nucleotides. The term nucleic acid includes deoxyribonucleic acid ("DNA") and ribonucleic acid ("RNA"). DNA may be in the form of anti-sense, plasmid DNA, parts of a plasmid DNA, vectors (P1, PAC, BAC, YAC, artificial chromosomes), expression cassettes, chimeric sequences, chromosomal DNA, or derivatives of these groups. RNA may be in the form of oligonucleotide RNA, tRNA (transfer RNA), snRNA (small nuclear RNA), rRNA (ribosomal RNA), mRNA (messenger RNA), anti-sense RNA, ribozymes, chimeric sequences, or derivatives of these groups. "Anti-sense" is a nucleic acid that interferes with the function of DNA and/or RNA. This may result in suppression of expression. Natural nucleic acids have a phosphate backbone, artificial nucleic acids may contain other types of backbones, nucleotides, or bases. These include PNAs (peptide nucleic acids), phosphothionates, and other variants of the phosphate backbone of native nucleic acids. In addition, DNA and RNA may be single, double, triple, or quadruple stranded. "Expression cassette" refers to a natural or recombinantly produced nucleic acid which is capable of expressing protein(s). A DNA expression cassette typically includes a promoter (allowing transcription initiation), and a sequence encoding one or more proteins. Optionally, the expression cassette may include transcriptional enhancers, non-coding sequences, splicing signals, transcription termination signals, and polyadenylation signals. An RNA expression cassette typically includes a translation initiation codon (allowing translation initiation), and a sequence encoding one or more proteins. Optionally, the expression cassette may include translation termination signals, a polyadenosine sequence, internal ribosome entry sites (IRES), and non-coding sequences.

Delivery of a nucleic acid means to transfer a nucleic acid from a container outside a mammal to near or within the outer cell membrane of a cell in the mammal. The term "transfection" may be used, in general, as a substitute for the term "delivery," or, more specifically, the transfer of a nucleic acid from directly outside a cell membrane to within the cell membrane. The transferred (or "transfected") nucleic acid may contain an expression cassette. If the nucleic acid is a primary RNA transcript that is processed into messenger RNA, a ribosome translates the messenger RNA to produce a protein within the cytoplasm. If the nucleic acid is a DNA, it enters the nucleus where it is transcribed into a messenger RNA that is transported into the cytoplasm where it is translated into a protein. Therefore if a nucleic acid expresses its cognate protein, then it must have entered a cell. A protein may subsequently be degraded into peptides, which may be presented to the immune system.

Polypeptide refers to a linear series of amino acid residues connected to one another by peptide bonds between the alpha-amino group and carboxyl group of contiguous amino acid residues.

"Protein" refers herein to a linear series of greater than 2 amino acid residues connected one to another as in a polypeptide. A "therapeutic" effect of the protein in attenuating or preventing the disease state can be accomplished by the protein either staying within the cell, remaining attached to the cell in the membrane, or being secreted and dissociated from the cell where it can enter the general circulation and blood. Secreted proteins that can be therapeutic include hormones, cytokines, growth factors, clotting factors, antiprotease proteins (e.g., alpha1-antitrypsin), angiogenic proteins (e.g., vascular endothelial growth factor, fibroblast growth factors), anti-angiogenic proteins (e.g., endostatin, angiostatin), and other proteins that are present in the blood. Proteins on the membrane can have a therapeutic effect by providing a receptor for the cell to take up a protein or lipoprotein (e.g., low density lipoprotein receptor). Therapeutic proteins that stay within the cell ("intracellular proteins") can be enzymes that clear a circulating toxic metabolite as in phenylketonuria. They can also cause a cancer cell to be less proliferative or cancerous (e.g., less metastatic), or interfere with the replication of a virus. Intracellular proteins can be part of the cytoskeleton (e.g., actin, dystrophin, myosins, sarcoglycans, dystroglycans) and thus have a therapeutic effect in cardiomyopathies and musculoskeletal diseases (e.g., Duchenne muscular dystrophy, limb-girdle disease). Other therapeutic proteins of particular interest to treating heart disease include polypeptides affecting cardiac contractility (e.g., calcium and sodium channels), inhibitors of restenosis (e.g., nitric oxide synthetase), angiogenic factors, and anti-angiogenic factors.

Biomolecule refers to peptides, polypeptides, proteins, enzymes, polynucleotides, oligonucleotides, viruses, antigens, carbohydrates (and congugates), lipids, and sacharides.

Enzymes are proteins evolved by the cells of living organisms for the specific function of catalyzing chemical reactions.

A chemical reaction can take place within the micelle and nucleic acid complex. A chemical reaction is defined as the formation or cleavage of covalent or ionic bonds. As a result of the chemical reaction a polymer can be formed. A polymer is defined as a compound containing more than two monomers. A monomer is a compound that can be attached to itself or another monomer and thus form a polymer. In one preferred embodiment the surfactant is polymerized by chain or step polymerization and then the. surfactant properties are destroyed. This destruction of the surfactant properties could be a accomplished by breaking a chemical bond and separating the hydrophilic and hydrophobic moieties.

A chemical reaction can be used to attach a gene transfer enhancing signal to the nucleic acid complex. The gene transfer enhancing signal (or abbreviated as the Signal) is defined in this specification as a molecule that modifies the nucleic acid complex and can direct it or the nucleic acid to a cell location (such as tissue) or location in a cell (such as the nucleus) either in culture or in a whole organism. By modifying the cellular or tissue location of the foreign gene, the expression of the foreign gene can be enhanced.

The gene transfer enhancing signal can be a protein, peptide, lipid, steroid, sugar, carbohydrate, (non-expressing) nucleic acid or synthetic compound. The gene transfer enhancing signals enhance cellular binding to receptors, cytoplasmic transport to the nucleus and nuclear entry or release from endosomes or other intracellular vesicles.

Nuclear localizing signals enhance the targeting of the gene into proximity of the nucleus and/or its entry into the nucleus. Such nuclear transport signals can be a protein or a peptide such as the SV40 large T ag NLS or the nucleoplasmin NLS. These nuclear localizing signals interact with a variety of nuclear transport factors such as the NLS receptor (karyopherin alpha) which then interacts with karyopherin beta. The nuclear transport proteins themselves could also function as NLS's since they are targeted to the nuclear pore and nucleus.

Signals that enhance release from intracellular compartments (releasing signals) can cause DNA release from intracellular compartments such as endosomes (early and late), lysosomes, phagosomes, vesicle, endoplasmic reticulum, golgi apparatus, trans golgi network (TGN), and sarcoplasmic reticulum. Release includes movement out of an intracellular compartment into cytoplasm or into an organelle such as the nucleus. Releasing signals include chemicals such as chloroquine, bafilomycin or Brefeldin A1. and the ER-retaining signal (KDEL sequence), viral components such as influenza virus hemagglutinin subunit HA-2 peptides and other types of amphipathic peptides.

Cellular receptor signals are any signal that enhances the association of the gene with a cell. This can be accomplished by either increasing the binding of the gene to the cell surface and/or its association with an intracellular compartment, for example: ligands that enhance endocytosis by enhancing binding the cell surface. This includes agents that target to the asialoglycoprotein receptor by using asiologlycoproteins or galactose residues. Other proteins such as insulin, EGF, or transferrin can be used for targeting. Peptides that include the RGD sequence can be used to target many cells. Chemical groups that react with sulfhydryl or disulfide groups on cells can also be used to target many types of cells. Folate and other vitamins can also be used for targeting. Other targeting groups include molecules that interact with membranes such as lipids fatty acids, cholesterol, dansyl compounds, and amphotericin derivatives. In addition viral proteins could be used to bind cells.

A polynucleotide can be delivered to a cell in order to produce a cellular change that is therapeutic. The delivery of polynucleotides or other genetic material for therapeutic purposes (the art of improving health in an animal including treatment or prevention of disease) is gene therapy. The polynucleotides are coded to express a whole or partial protein, or may be anti-sense, and can be delivered either directly to the organism in situ or indirectly by transfer to a cell that is then transplanted into the organism. The protein can be missing or defective in an organism as a result of genetic, inherited or acquired defect in its genome. For example, a polynucleotide may be coded to express the protein dystrophin that is missing or defective in Duchenne muscular dystrophy. The coded polynucleotide is delivered to a selected group or groups of cells and incorporated into those cell's genome or remain apart from the cell's genome. Subsequently, dystrophin is produced by the formerly deficient cells. Other examples of imperfect protein production that can be treated with gene therapy include the addition of the protein clotting factors that are missing in the hemophilia's and enzymes that are defective in inborn errors of metabolism such as phenylalanine hydroxylase. A delivered polynucleotide can also be therapeutic in acquired disorders such as neurodegenerative disorders, cancer, heart disease, and infections. The polynucleotide. has its therapeutic effect by entering the cell. Entry into the cell is required for the polynucleotide to produce the therapeutic protein, to block the production of a protein, or to decrease the amount of a RNA.

A therapeutic effect of the protein in attenuating or preventing the disease state can be accomplished by the protein either staying within the cell, remaining attached to the cell in the membrane or being secreted and dissociating from the cell where it can enter the general circulation and blood. Secreted proteins that can be therapeutic include hormones, cytokines, growth factors, clotting factors, anti-protease proteins (e.g. alpha-antitrypsin) and other proteins that are present in the blood. Proteins on the membrane can have a therapeutic effect by providing a receptor for the cell to take up a protein or lipoprotein. For example, the low density lipoprotein (LDL) receptor could be expressed in hepatocytes and lower blood cholesterol levels and thereby prevent atherosclerotic lesions that can cause strokes or myocardial infarction. Therapeutic proteins that stay within the cell can be enzymes that clear a circulating toxic metabolite as in phenylketonuria. They can also cause a cancer cell to be less proliferative or cancerous (e.g. less metastatic). A protein within a cell could also interfere with the replication of a virus.

The delivered polynucleotide can stay within the cytoplasm or nucleus apart from the endogenous genetic material. Alternatively, the polynucleotide could recombine (become a part of) the endogenous genetic material. For example, DNA can insert into chromosomal DNA by either homologous or non-homologous recombination.

Parenchymal cells are the distinguishing cells of a gland or organ contained in and supported by the connective tissue framework. The parenchymal cells typically perform a function that is unique to the particular organ. The term "parenchymal" often excludes cells that are common to many organs and tissues such as fibroblasts and endothelial cells within the blood vessels. In a liver organ, the parenchymal cells include hepatocytes, Kupffer cells and the epithelial cells that line the biliary tract and bile ductules. The major constituent of the liver parenchyma are polyhedral hepatocytes (also known as hepatic cells) that presents at least one side to an hepatic sinusoid and apposed sides to a bile canaliculus. Liver cells that are not parenchymal. cells include cells within the blood vessels such as the endothelial cells or fibroblast cells.

In striated muscle, the parenchymal cells include myoblasts, satellite cells, myotubules, and myofibers. In cardiac muscle, the parenchymal cells include the myocardium also known as cardiac muscle fibers or cardiac muscle cells and the cells of the impulse connecting system such as those that constitute the sinoatrial node, atrioventricular node, and atrioventricular bundle. In a pancreas, the parenchymal cells include cells within the acini such as zymogenic cells, centroacinar cells, and basal or basket cells and cells within the islets of Langerhans such as alpha and beta cells. In spleen, thymus, lymph nodes and bone marrow, the parenchymal cells include reticular cells and blood cells (or precursors to blood cells) such as lymphocytes, monocytes, plasma cells and macrophages.

In the nervous system which includes the central nervous system (the brain and spinal cord) peripheral nerves, and ganglia, the parenchymal cells include neurons, glial cells, microglial cells, oligodendrocytes, Schwann cells, and epithelial cells of the choroid plexus. In the kidney, parenchymal cells include cells of collecting tubules and the proximal and distal tubular cells. In the prostate, the parenchyma includes epithelial cells. In glandular tissues and organs, the parenchymal cells include cells that produce hormones. In the parathyroid glands, the parenchymal cells include the principal cells (chief cells) and oxyphilic cells. In the thyroid gland, the parenchymal cells include follicular epithelial cells and parafollicular cells. In the adrenal glands, the parenchymal cells include the epithelial cells within the adrenal cortex and the polyhedral cells within the adrenal medulla. In the parenchyma of the gastrointestinal tract such as the esophagus, stomach, and intestines, the parenchymal cells include epithelial cells, glandular cells, basal, and goblet cells. In the parenchyma of lung, the parenchymal cells include the epithelial cells, mucus cells, goblet cells, and alveolar cells. In fat tissue, the parenchymal cells include adipose cells or adipocytes. In the skin, the parenchymal cells include the epithelial cells of the epidermis, melanocytes, cells of the sweat glands, and cells of the hair root. In cartilage, the parenchyma includes chondrocytes. In bone, the parenchyma includes osteoblasts, osteocytes, and osteoclasts. Intravascular refers to an intravascular route of administration that enables a polymer, oligonucleotide, or polynucleotide to be delivered to cells more evenly distributed and more efficiently than direct injections.

Intravascular herein means within an internal tubular structure called a vessel that is connected to a tissue or organ within the body of an animal, including mammals. Within the cavity of the tubular structure, a bodily fluid flows to or from the body part. Examples of bodily fluid include blood, lymphatic fluid, or bile. Examples of vessels include arteries, arterioles, capillaries, venules, sinusoids, veins, lymphatics, and bile ducts. The intravascular route includes delivery through the blood vessels such as an artery or a vein. "Intracoronary" refers to an intravascular route for delivery to the heart wherein the blood vessels are the coronary arteries and veins.

Permeability is defined herein as the propensity for macromolecules such as nucleic acids to move through vessel walls and enter the extravascular space. One measure of permeability is the rate at which macromolecules move through the vessel wall and out of the vessel. Another measure of permeability is the lack of force that resists the movement through the vessel wall and out of the vessel. Vessels contain elements that prevent macromolecules from leaving the intravascular space (internal cavity of the vessel). These elements include endothelial cells and connective material (e.g., collagen). High permeability indicates that there are fewer of these elements that can block the egress of macromolecules and that the spaces between these elements are larger and more numerous. In this context, high permeability enables a high percentage of nucleic acids being delivered to leave the intravascular space, while low permeability indicates that a low percentage of the nucleic acids will leave the intravascular space.

The permeability of a blood vessel can be increased by increasing the intravascular hydrostatic pressure. In a preferred embodiment, the intravascular hydrostatic pressure is increased by rapidly (from 1 seconds to 30 minutes) injecting a nucleic acid in solution into the blood vessel, which increases the hydrostatic pressure. In another preferred embodiment, hydrostatic pressure is increased by obstructing the outflow of the injection solution from the tissue for a period of time sufficient to allow delivery of a nucleic acid. Obstructing means to block or impede the outflow of injection fluid, thereby transiently (reversibly) blocking the outflow of the blood. Furthermore, rapid. injection may be combined with obstructing the outflow in yet another preferred embodiment. For example, an afferent vessel supplying an organ is rapidly injected while the efferent vessel draining the tissue is blocked transiently (e.g., by ligation, or by an inflated intravascular balloon). The efferent vessel (also called the venous outflow or tract) draining outflow from the tissue is partially or totally clamped for a period of time sufficient to allow delivery of a nucleic acid. In the reverse, an efferent vessel is injected while the corresponding afferent vessel is occluded.

An administration route involving the mucosal membranes is meant to include nasal, bronchial, inhalation into the lungs, or via the eyes.

Transdermal refers to application to mammal skin in which drug delivery occurs by crossing the dermal layer.

Crosslinking refers to the chemical attachment of two or more molecules with a bifunctional reagent. A bifunctional reagent is a molecule with two reactive ends. The reactive ends can be identical as in a homobifunctional molecule, or different as in a heterobifucnctional molecule.

Electrostatic interactions are the non-covalent association of two or more substances due to attractive forces between positive and negative charges.

Amphipathic compounds have both hydrophilic (water-soluble) and hydrophobic (water-insoluble) parts.

A polycation is a polymer containing a net positive charge, for example poly-L-lysine hydrobromide. The polycation can contain monomer units that are charge positive, charge neutral, or charge negative, however, the net charge of the polymer must be positive. A polycation also can mean a non-polymeric molecule which contains two or more positive charges. A polyanion is a polymer containing a net negative charge, for example polyglutamic acid. The polyanion can contain monomer units that are charge negative, charge neutral, or charge positive, however, the net charge on the polymer must be negative. A polyanion can also mean a non-polymeric molecule that contains. two or more negative charges. The term polyion includes polycation, polyanion, zwitterionic polymers, and neutral polymers. The term zwitterionic refers to the product (salt) of the reaction between an acidic group and a basic group that are part of the same molecule.

Mixing means the method of interdispursing two or more solvents, or solvent(s) and solute(s). Sonication and agitation are forms of mixing. Solvent refers to a material in the liquid phase that can be used to solubilize (dissolve) a compound. Solute refers to a compound dissolved in a solvent.

Hydrocarbon means containing carbon and hydrogen atoms; and halohydrocarbon means containing carbon, halogen (F, Cl, Br, I), and hydrogen atoms.

Alkyl means containing sp3 hybridized carbon atoms; alkenyl means containing two or more sp2 hybridized carbon atoms; aklkynyl means containing two or more sp hybridized carbon atoms; aralkyl means containing one or more aromatic ring(s) in addition containing sp3 hybridized carbon atoms; aralkenyl means containing one or more aromatic ring(s) in addition to containing two or more sp2 hybridized carbon atoms; aralkynyl means containing one or more aromatic ring(s) in addition to containing two or more sp hybridized carbon atoms; steroid includes natural and unnatural steroids and steroid derivatives. A steroid derivative means a sterol, a sterol in which the hydroxyl moiety has been modified (for example, acylated), or a steroid hormone, or an analog thereof; carbohydrates include natural and unnatural sugars (for example glucose), and sugar derivatives (a sugar derivative means a system in which one or more of the hydroxyl groups on the sugar moiety has been modified (for example acylated), or a system in which one or more of the hydroxyl groups is not present); polyoxyethylene means a polymer having two to six (n=2–6) ethylene oxide units (—(CH2CH2O)n-) or a derivative thereof; and R not identified by number is meant to be any compatible group, for example alkyl, alkenyl, alkynyl, aralkyl, aralkenyl, or aralkynyl, and can include heteroatoms (N, O, S), and carbonyl groups.

Hydrophilic groups indicate in qualitative terms that the chemical moiety is water-preferring. Typically, such chemical groups are water soluble, and are hydrogen bond donors or acceptors with water. Examples of hydrophilic groups include compounds. with the following chemical moieties carbohydrates; polyoxyethylene, peptides, oligonucleotides and groups containing amines, amides, alkoxy amides, carboxylic acids, sulfurs, or hydroxyls. Hydrophobic groups indicate in qualitative terms that the chemical moiety is water-avoiding. Typically, such chemical groups are not water soluble, and tend not to hydrogen bond. Hydrocarbons are hydrophobic groups.

The terms "therapeutic" and "therapeutic results" are defined in this application as levels of gene products, including reporter (marker) gene products, which indicate a reasonable expectation of gene expression using similar compounds (other nucleic acids including other genes), at levels considered sufficient by a person having ordinary skill in the art of gene therapy. For example: Hemophilia A and B are caused by deficiencies of the X-linked clotting factors VIII and IX, respectively. Their clinical course is greatly influenced by the percentage of normal serum levels of factor VIII or IX: <2%, severe; 2–5%, moderate; and 5–30% mild. This indicates that in severe patients only 2% of the normal level can be considered therapeutic. Levels greater than 6% prevent spontaneous bleeds but not those secondary to surgery or injury. A person having ordinary skill in the art of gene therapy would reasonably anticipate therapeutic levels of expression of a gene specific for a disease based upon sufficient levels of marker gene results. In the Hemophilia example, if marker genes were expressed to yield a protein at a level comparable in volume to 2% of the normal level of factor VIII, it can be reasonably expected that the gene coding for factor VIII would also be expressed at similar levels.

There are three types of reporter (marker) gene products that are expressed from reporter genes. The reporter gene/protein systems include:

a) Intracellular gene products such as luciferase, β-galactosidase, or chloramphenicol acetyl transferase. Typically, they are enzymes whose enzymatic activity can be easily measured.

b) Intracellular gene products such as β-galactosidase or green fluorescent protein which identify cells expressing the reporter gene. On the basis of the intensity of cellular staining, these reporter gene products also yield qualitative information concerning the amount of foreign protein produced per cell.

Secreted gene products such as growth hormone, factor IX, or alpha1-antitrypsin are useful for determining the amount of a secreted protein that a gene transfer procedure can produce. The reporter gene product can be assayed in a small amount of blood.

EXAMPLES

Compound Preparation:
Synthesis of (-D-Glucopyranosyl Dodecane Disulfide
To a solution of dodecane thiol (1.00 mL, 4.17 mmol, Aldrich) in 20 mL CHCl3 was added sulfuryl chloride (0.74 mL, 9.18 mmol, Aldrich), and the resulting mixture was stirred at room temperature for 18 h. Removal of solvent (aspirator), afforded dodecansulfenyl chloride that was determined to be sufficiently pure by 1H NMR.

To a solution of dodecansulfenyl chloride (213 mg, 0.899 mmol) in 2.7 mL acetonitrile was added (-D-thioglucose sodium salt (200. mg, 0,917 mmol, Aldrich) and 15-crown-5 (0.18 mL, 0.899 mmol, Aldrich). The resulting mixture was stirred at ambient temperature for 3 h, and the solvent removed (aspirator). The residue was triturated with CHCl3 and filtered. The residue was purified by flash column chromatography on silica gel (0–5% MeOH in CH2Cl2). Crystallization (EtOAc) afforded 85 mg (24%) of a fine white solid.

I. Example 1

Synthesis of β-D-Glucopyranosyl Dodecane Disulfide

To a solution of dodecane thiol (1.00 mL, 4.17 mmol, Aldrich Chemical Company) in 20 mL CHCl3 was added sulfuryl chloride (0.74 mL, 9.18 mmol, Aldrich Chemical Company), and the resulting mixture was stirred at room temperature for 18 h. Removal of solvent (aspirator), afforded dodecansulfenyl chloride that was determined to be sufficiently pure by 1H NMR.

To a solution of dodecansulfenyl chloride (213 mg, 0.899 mmol) in 2.7 mL acetonitrile was added 1-thio-β-D-glucose sodium salt hydrate (200. mg, 0,917 mmol, Aldrich Chemical Company) and 15-crown-5 (0.18 mL, 0.899 mmol, Aldrich Chemical Company). The resulting mixture was stirred at ambient temperature for 3 h, and the solvent removed (aspirator). The residue was triturated with CHCl3 and filtered. The residue was purified by flash column chromatography on silica gel (0–5% MeOH in CH2Cl2). Crystallization (EtOAc) afforded 85 mg (24%) of β-D-glucopyranosyl dodecane disulfide as a fine white solid.

Example 2

Demonstration of Micelle Formation with β-D-Glucopyranosyl Dodecane Disulfide, and Micelle Destruction with Dithiothreitol To a solution of β-D-Glucopyranosyl dodecane disulfide (10 mg) in 1 mL CD3Cl was added 1 mL H2O. The sample was rapidly mixed resulting in a thick white emulsion. After 18 h, the organic and aqueous layers were emulsified to approximately 95%. After 4 d, the organic and aqueous layers remained emulsified to approximately 70%. To a 1 mL portion of the emulsion was added 60 μg of dithiothreitol (Aldrich Chemical Company), and the solution was mixed. After 30 min, the emulsion had cleared. 5,5'-Dithiobis(2-nitrobenzioc acid) (1 mg, Aldrich Chemical Company) was added, resulting in a yellow solution, verifying the presence of free sulfide. Analysis also indicated the presence of dodecane thiol and 1-thio-β-D-glucose by TLC.

Example 3

Solubilization of PCILuc DNA in Reversed Micelles

Procedure:

PCILuc DNA (pDNA) (Zhang, G., Vargo, D., Budker, V., Armstrong, N., Knechtle, S., Wolff, J. A. Human Gene Therapy, 8, 1763–1772, 1997) (11 μg) was taken up in a solution (3–67 μL) of HEPES (25 mM, pH 7.8) and EDTA (0.5 mM). Polyoxyethylene(4) lauryl ether (Brij 30) (1.2 mL, Aldrich Chemical Company) was taken up in 2,2,4-trimethylpentane (TMP) (8.8 mL, Aldrich Chemical Company). To the Brij 30/TMP solution (0.7 mL) was added the pDNA in buffer (3–67 μL). The mixtures were shaken (2 min) resulting in clear solutions. After 10 min the turbidity was determined utilizing a fluorescence spectrophotometer (Hitachi, model F3010, extinction/emission wavelength of 529 nm). W0 is defined as the molar ratio of water to surfactant.

Results:

| H2O (μL) | W0 | Turbidity (529 nm) |
|---|---|---|
| 0 | 0 | 19 |
| 3 | 0.72 | 49 |
| 7 | 1.68 | 63 |
| 12 | 2.87 | 63 |

-continued

| H2O (μL) | W0 | Turbidity (529 nm) |
|---|---|---|
| 17 | 4.07 | 82 |
| 27 | 6.46 | 2764 |
| 47 | 11.25 | 1565 |
| 67 | 16.04 | 214 |

Analysis:

At 20° C., the pDNA solution when added to the Brij 30/TMP forms inversed micelles for an aqueous content of up to W0=4. For a solution of Brij 30 in dodecane the hydrophile-lipophile balance (HLB) temperature has been determined to be approximately 29.2° C. (Kunieda, H. Langmuir 7,1915, 1991). For the present system it was shown that below 29.2 ~C, w/o microemulsion are present for a W0 of less then 10. By increasing the water content, one obtains a two-phase system and then a lamellar phase. In the case of Brij 30 in TMP, a two-phase system appears at W0 of more then 6 and a lamellar phase at W0 of more then 11.

Example 4

Determination of the Size of PCILuc DNA Contained in Inversed Micelles

Part A. Centrifugation.

Procedure:

PCILuc DNA (pDNA) (Zhang, G., Vargo, D., Budker, V., Armstrong, N., Knechtle, S., Wolff, J. A. Human Gene Therapy, 8, 1763–1772, 1997) (36 μg) was taken up in a solution of HEPES (25 mM, pH 7.8) and EDTA (0.5 mM) (10 μL, 20 μL, 30 μL, and 50 μL). The resulting solutions were added to a mixture of Polyoxyethylene(4) lauryl ether (Brij 30) (Aldrich Chemical Company)/2,2,4-trimethylpentane (TMP) (Aldrich Chemical Company) (1 mL, 1:7.3 v/v) and agitated. The UV adsorption was determined (Perkin Elmer, UV/VIS Spectrophotometer, model Lambda 6) against 10 μL of HEPES (25 mM, pH 7.8) and EDTA (0.5 mM) buffer in Brij 30/TMP (1 mL, 1:7.3 v/v). The samples were centrifuged 5 min at 15000 rpm and the UV adsorption was again determined.

| Conditions | W0 | $A_{260}$ before centrifugation | $A_{260}$ after centrifugation |
|---|---|---|---|
| DNA in buffer | — | 1.07 | 1.07 |
| 10 μl | 1.68 | 1.07 | 1.11 |
| 20 μl | 3.36 | 0.99 | 1.14 |
| 30 μl | 5.04 | 0.97 | 1.01 |
| 50 μl | 8.39 | 2.44 | ND[a] |

[a]UV absorption not determined. Solution was two-phase.

Analysis:

At 20° C., micelles that contain pDNA (up to W0=5) are small enough to stay in solution in the course of centrifugation. For these solutions, no change in the UV absorption spectra was recorded as compared to the UV absorption of pDNA in HEPES (25 mM, pH 7.8) and EDTA (0.5 mM).

Part B. Particle Size of Micelles without PCILuc DNA.

Procedure:

A solution (5–50 μL) of HEPES (25 mM, pH 7.8) and EDTA (0.5 mM) was added to a mixture of Brij 30/TMP (1 mL, 1:7.3 v/v) and agitated (2 min). The samples were centrifuged (1 min) at 12000 rpm and the size of micelles measured (Particle Sizer, Brookhaven Instrument Corporation).

Results:

| Volume of buffer (μL) | W0 | Size nm |
|---|---|---|
| 0 | 0 | 1.3 |
| 5 | 0.84 | 2.9 |
| 10 | 1.68 | 3.4 |
| 20 | 3.35 | 5.1 |
| 30 | 5.04 | 9.7 |
| 50 | 8.39 | indefinite |

Analysis:

The size of the micelles changes proportionally as the water content increases, from 1.3 nm for "dry" micelles to 9.7 nm for micelles with W0=5. At a higher water content, a two-phase system is present.

Part C. Particle Size of Micelles Containing PCILuc DNA.

Procedure:

A solution pDNA in HEPES (25 mM, pH 7.8) and EDTA (0.5 mM) was added to a mixture of Brij 30/TMP (1 mL, 1:7.3 v/v) and agitated (2 min) to form micelles with a WO of 3.35. The samples were centrifuged (1 min) at 12000 rpm and the size of micelles was measured (Particle Sizer, Brookhaven Instrument Corporation).

Results:

| DNA ng | Small micelles (nm) | Large micelles (nm) |
|---|---|---|
| 0 | 5.1 | — |
| 40 | 4.0 | 16.2 |
| 80 | 4.7 | 48.7 |
| 120 | 4.7 | 62.8 |
| 160 | 4.4 | 51.7 |

Analysis:

Two types of micelles appear to be present in the samples. There are small, "empty" micelles, and large pDNA containing micelles. It appears that the size of micelles containing pDNA increases as the concentration of pDNA increases. The micelle appears to be saturated at a size of 50–60 nm.

Example 5

Conformation of PCILuc DNA in Inverse Micelles

Procedure:

pDNA (60 μg) was taken up in 10 mM potassium phosphate buffer at pH 7.5 (20 μL and 60 μL). The pDNA solutions were added to a mixture of Brij 30/TMP (1 mL, 1:7.3 v/v) and agitated (2 min). The circular dichroism spectra were measured for each sample (cell length=0.5 cm, Spectropolarimeter 62DS, Avive Associates) at 30° C. against control samples prepared without the pDNA (FIG. 1, the ellipticity value for the control samples were subtracted from the experimental samples).

Figure 1:
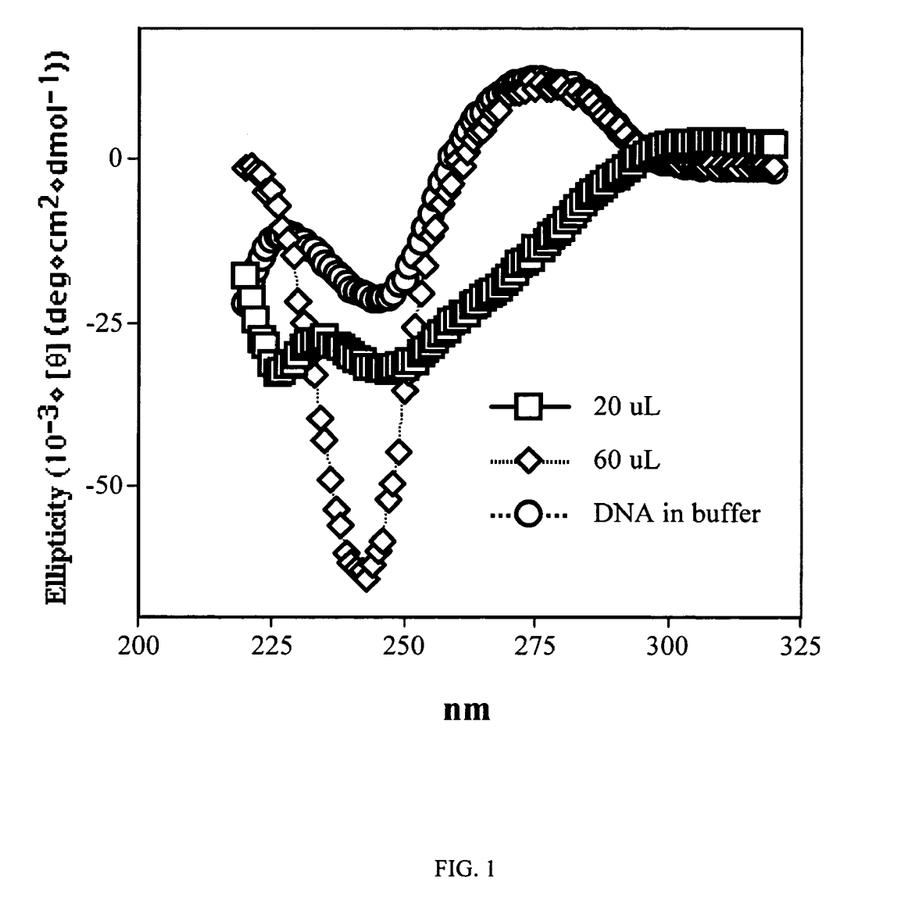
FIG. 1. Circular dichroism spectra measured for samples of plasmid DNA added to a mixture of Brij30/TMP or DNA alone at 30° C. The ellipticity value for control samples prepared without DNA were subtracted from the experimental samples.

Results:

There are shifts in the position of both the positive and negative bands and in the position of the cross-over point for the 20 μL pDNA solution (W0=3.35). Spectra that are similarly shifted are broadly defined as -spectra, and are attributed to a condensed form of pDNA. In contrast the spectra of the 60 μL pDNA solution (W0=10.05) resembles the spectra of DNA in buffer alone in respect to cross-over point. However this spectra is characterized by an increase in the intensity of the negative band (maximum at 240 nm).

Example 6

PCILuc DNA Condensation

Part A. Ethidium Bromide.

Procedure:

A solution of pDNA in HEPES (25 mM, pH 7.8) and EDTA (0.5 mM) (3–67 μL) containing ethidium bromide (0.9 μg, Sigma Chemical Company) was added to a mixture of Brij 30/TMP (0.7 mL, 1:7.3 v/v) and agitated. After 4 h at ambient temperature, the samples were assayed utilizing a fluorescence spectrophotometer (Hitachi, Model F-3010), with an excitation wavelength of 525 nm and an emission wavelength of 595 nm.

Results:

| Volume (μL) | W0 | I/Imax*100 |
|---|---|---|
| 3 | 0.72 | 15 |
| 7 | 1.68 | 13 |
| 12 | 2.87 | 12 |
| 17 | 4.07 | 12.5 |
| 27 | 6.46 | 23 |
| 47 | 11.25 | 35 |
| 67 | 16.04 | 51 |

Analysis:

The pDNA in reverse micelles of up to W0=4 is condensed. Additionally, some level of condensation is shown for micelles up to W0=16.

Part B: Determination of Rhodamine Labeled DNA Condensation in a Reverse Micelle.

Procedure:

pDNA was modified to a level of 1 Rhodamine per 100 bases using Mirus' Label It® Rhodamine kit (Rhodamine Containing DNA Labeling Reagent, Mirus Corporation). The modified pDNA (2.5 μg) was solubilized in different volumes of HEPES (25 mM, pH 7.8) and EDTA (0.5 mM) and added to a solution of Brij 30/TMP (0.7 mL, 1:7.3 v/v), and agitated. The fluorescence was determined using a fluorescence spectrophotometer (Hitachi, Model F-3010), at an excitation wavelength of 591 nm, and an emission wavelength of 610 nm.

Results:

| Buffer Volume (µL) | W0 | ($I_{610}$ sample/$I_{610}$ DNA in buffer)*100 |
|---|---|---|
| 2 | 0.48 | 104 |
| 4 | 0.96 | 80 |
| 5 | 1.2 | 34 |
| 10 | 2.39 | 31 |
| 12 | 2.87 | 24 |
| 15 | 3.59 | 33 |
| 22 | 5.26 | 32 |
| 32 | 7.66 | 65 |
| 42 | 10.0 | 106 |
| 52 | 12.45 | 93 |
| 62 | 14.84 | 78 |

It should be noted that around W0=10 turbidity has significant contribution in fluorescence. The assay indicates that under low water conditions, pDNA does not appear to be condensed. As the amount of water in the system is increased, the fluorescence results indicate that pDNA is condensed within the w/o microemulsion.

II. Example 7 pDNA Condensation in Reverse Micelles

Procedure:

pDNA was modified to a level of 1 Rhodamine per 100 bases using standard procedures (Label It®, Mirus Corporation). Labeled pDNA (various amounts) was taken up in HEPES (25 mM, pH 7.8) EDTA (0.5 mM) (various amounts) and was mixed with unmodified pDNA (various amounts) to afford 2.5 µg total of pDNA. The resulting solution was added to Brij 30/TMP (0.7 mL, 1:7.3 v/v) and the fluorescence was determined using a fluorescence spectrophotometer (Hitachi, Model F-3010), at an excitation wavelength of 591 nm, and an emission wavelength of 610 nm. For comparison, the fluorescence was also determined for the similar ratios of Rh-labeled pDNA/pDNA containing 2 mM spermidine (Sigma Chemical Company) in HEPES (25 mM, pH 7.8) and EDTA (0.5 mM) (0.7 mL).

Results:

| | | % of Fluorescence quenching | | |
|---|---|---|---|---|
| % Rh-DNA | W0 = 2.39 | W0 = 3.59 | W0 = 7.18 | 2 mM Sp. |
| 100 | 68.8 | 61.2 | 41.3 | 69.8 |
| 76 | 65.9 | 57.5 | 33.1 | 61 |
| 51 | 59 | 52.2 | 30 | 48 |
| 26 | 55.5 | 50.4 | 28.3 | 26.1 |

Analysis:

The fluorescence data indicates a relatively weak affect of Rh-labeled pDNA dilution by unlabeled pDNA. On the other hand, in the samples containing spermidine, a strong effect of the Rh-pDNA dilution by unlabeled DNA is shown. In reverse micelles, the pDNA condensation starts from monomolecular condensation and therefore show little effect by the dilution protocol. However, in the spermidine containing systems (non-micellular) the strong effect indicates that condensation is multimolecular.

III. Example 8

Transmission Electron Microscope Assay

Procedure:

A drop of Poly-L-lysine (PLL) (30–70 KD, Sigma Chemical Company) in water (concentration of 10 mg/mL) was placed on a covered EM grid. The solution was removed, and the grid was dried. A drop of 2,2,4-trimethylpentane (TMP) (Aldrich Chemical Company) in various amounts of HEPES (25 mM, pH 7.8) and EDTA (0.5 mM) both with and without PCILuc DNA (pDNA) (7 µg/mL TMP) was placed on the grid.

After 5 min, the solution was removed and the grid was washed with TMP (3×) and water (1×), and then stained with Uranyl Acetate.

Results:

Samples containing 20 or 60 µL of HEPES (25 mM, pH 7.8) and EDTA (0.5 mM) in TMP (1 mL) failed to show any structures. A sample containing pDNA (7 µg) in HEPES (25 mM, pH 7.8) and EDTA (0.5 mM) in TMP (1 mL) also failed to show any structures. A sample containing pDNA in HEPES (25 mM, pH 7.8) and EDTA (0.5 mM) (20 µL) and TMP (1 mL) demonstrated ring like structures with an external diameter of 59.8±12.5 nm and an internal diameter of 32.9±12.1 nm. A sample of pDNA in HEPES (25 mM, pH 7.8) and EDTA (0.5 mM) (60 µL) and TMP (1 mL) demonstrated long threads with a 7–12 nm diameter. The volume of the terroid ring $V=(^2/_4)(R_{out}-R_{in})^2 (R_{out}+R_{in})$ equal $41*10^3$ nm$^3$. The volume of "dry" PCILuc DNA is $6.4*10^3$ nm$^3$. With consideration of packing parameter every toroid therefore contains five pDNA's.

Example 9

PCILuc DNA/Labeled Poly-L-Lysine Interaction

Procedure:

To Poly-L-lysine (PLL) (4 mg, Sigma Chemical Company) in potassium phosphate buffer (pH 8, 0.1 mL) was added 7-Chloro-4-nitrobenz-2-oxa-1,3-diazole (NBD-Cl) (0.4 mg, Sigma Chemical Company). The solution was heated at 37˜C for 2 h, cooled, and purified by gel-filtration on Sephadex G-25. The fluorescence was determined (Hitachi, model F-3010, excitation wavelength=466 nm, emission wavelength=540 nm), and the level of modification was estimated to be 5%. To the NBD-PLL (5 µg) in HEPES (25 mM, pH 7.8) and EDTA (0.5 mM) (1 mL), was added pDNA, and the fluorescence was again determined.

Results:

| pDNA µg | 0 | 1 | 2 | 4 | 6 |
|---|---|---|---|---|---|
| $I_{540}$ | 41 | 27 | 21 | 17 | 16 |

Analysis:

The interaction of the NBD-PLL with pDNA was shown to substantially decrease the quantum yield of fluorescence.

Example 10

PCILuc DNA/Polycation Interaction in a Reverse Micelle

Procedure:

NBD-PLL (example 9) was mixed with Polyoxyethylene (4) lauryl ether (Brij 30) (Aldrich Chemical Company)/2,2,4-trimethylpentane (TMP) (Aldrich Chemical Company) (1:7.3 v/v), and then mixed with an equal volume of Brij 30/TMP (1:7.3 v/v) that contained either HEPES (25 mM, pH 7.8) and EDTA (0.5 mM) or HEPES (25 mM, pH 7.8) and EDTA (0.5 mM) with pDNA (various amounts) After 10 min at ambient temperature, the fluorescence was determined for each sample.

| Conditions | $I_{540}$ |
|---|---|
| 0.5 mL TMPD with 5 µg NBD-PLL in 20 µL buffer + 0.5 mL TMPD with 20 µL buffer | 87 |
| 0.5 mL TMPD with 5 µg NBD-PLL in 20 µL buffer + 0.5 mL TMPD with 3.7 µg DNA in 20 µL buffer | 64 |
| 0.5 mL TMPD with 5 µg NBD-PLL in 20 µL buffer + 0.5 mL TMPD with 11.1 µg DNA 20 µL buffer | 38 |

Analysis:

The results from the fluorescence study indicate that pDNA in reverse micelles can interact with PLL also in reverse micelles.

IV. Example 11

PCILuc DNA/Crosslinked Polycation Interaction

Procedure:

To a solution of pDNA (35 µg) in HEPES (25 mM, pH 7.8), EDTA (0.5 mM), and NaCl (100 mM) (24 µL) was added Polyoxyethylene(4) lauryl ether (Brij 30) (Aldrich Chemical Company)/2,2,4-trimethylpentane (TMP) (Aldrich Chemical Company) (510 µL, 1:7.3 v/v). Poly-L-lysine (PLL) (95 µg, Sigma Chemical Company) in HEPES (25 mM, pH 7.8), EDTA (0.5 mM), and NaCl (100 mM) (12 µL) was added to Brij 30/TMP (290 µL, 1:7.3 v/v). The resulting solutions were mixed and heated to 40˜C for 30 min at which time Dimethyl 3,3'-dithiobispropionimidate-2HCl (DTBP, Pierce Chemical Company) in DMSO (various amounts of a 29.5 mg/mL solution) were added. The solution was heated to 40˜C for 25 min at which time HEPES (25 mM, pH 7.8), EDTA (0.5 mM), and NaCl (100 mM) (200 µL) was added, followed by EtOH (50 µL) and EtOAc (0.5 mL). After mixing and centrifugation, the aqueous layer was washed with EtOAc (2×1 mL) and Ether (2×1 mL). The samples were spun (5 min, 12000 rpm) and dialyzed for 16 h against HEPES (25 mM, pH 7.8) and NaCl (100 mM). The UV absorption was determined (Perkin Elmer UV/VIS Spectrophotometer, Model Lambda 6). A solution of TO6 (Zeng, Z., Clark, S. M., Mathies, R. A., Glazer, A. N. Analytical Biochemistry, 252, 110–114, 1997) (2 µL, 0.5 mg/mL in water) was added and the fluorescence was determined (Hitchi, Model F-3010, excitation wavelength=509 nm, emission wavelength=540 nm).

Results:

| # | Amount of DTBP µl | % DNA recovery | Fluorescence |
|---|---|---|---|
| 35 µg DNA (no treatment) | — | 100 | 120.4 |
| 1 | 0 | 3 | 0.275 |
| 2 | 3 | 14 | 1.76 |
| 3 | 6 | 19 | 3.07 |
| 4 | 12 | 24 | 4.02 |

Analysis:

The results indicate that the pDNA-PLL complex can be partly extracted from reverse micelles after the PLL has been crosslinked with DTBP. The pDNA in the extracted complexes is compacted because it does not interact with the fluorescent intercolator TO6.

Example 12

PCILuc DNA/Polyethylenimine Complexes in Reverse Micelles

Procedure:

pDNA was labeled as above (Label It®, Mirus Corporation). Labeled pDNA (14 µg) was taken up in HEPES (25 mM, pH 7.8) and EDTA (0.5 mM) (various amounts) and added to Polyoxyethylene(4) lauryl ether (Brij 30) (Aldrich Chemical Company)/2,2,4-trimethylpentane (TMP) (Aldrich Chemical Company) (1 mL, 1:7.3 v/v). The fluorescence and turbidity of each sample was determined. Polyethylenimine (PEI) (30 µg, Sigma Chemical Company) in HEPES (25 mM, pH 7.8) and EDTA (0.5 mM) (3 µL) was added to each sample. After 30 min the florescence and turbidity of each sample was determined.

Results:

|  | No PEI | | With PEI | |
|---|---|---|---|---|
|  | $I_{610}$ | Turbidity | $I_{610}$ | Turbidity |
| DNA in buffer | 28.45 | 31 | 8.7 | 76 |
| $W_0$ = 0.67 | 14.8 | 105 | 11.5 | 164 |
| 1.51 | 9.7 | 103 | 10.2 | 144 |
| 2.35 | 11.0 | 85 | 11.8 | 114 |
| 4.03 | 18.3 | 105 | 15.9 | 137 |
| 5.71 | 26.0 | 182 | 18.0 | 217 |
| 9.06 | 31.6 | 4200 | 17.8 | 4734 |

Analysis:

The decrease in fluorescence after the addition of PEI indicates that PEI was within the same micelle as the DNA and was bound to it.

Example 13

Oxidation within a Reverse Micelle

Procedure:

Cysteine Label IT® was prepared by amidation of amino Label IT® (Mirus Corporation Madison Wis.) with N-Boc-S-trityl cysteine (Sigma Chemical Company) utilizing dicyclohexylcarbodiimide (Aldrich Chemical Co.) as the coupling agent. The product was purified by precipitation with diethyl ether. The trityl and Boc protecting groups were removed with trifluoroacetic acid. The resulting free thiol group was protected with Aldrithiol-2® (Aldrich Chemical Co.) as the pyridyldithio mixed disulfide and was purified by diethyl ether precipitation and confirmed by mass spectrometry (Sciex API 150EX).

PCILuc DNA (pDNA) (Zhang, G., Vargo, D., Budker, V., Armstrong, N., Knechtle, S., Wolff, J. A. Human Gene Therapy, 8, 1763–1772, 1997) was modified with Cysteine Label IT® at weight ratios of 0.1:1 and 0.2:1 (reagent:DNA) at 37° C. for 1 hour. The labeled DNA was purified by ethanol precipitation. The purified DNA was reconstituted in 20 mM MOPS pH 7.5, 0.1 mM EDTA buffer at a final concentration of 1 μg/μL. The level of PDP-cysteine reagent incorporation on DNA was estimated from the optical adsorption ratio of pyridine-2-thione (λmax 343 nm and extinction coefficient E=8.08×10$^3$) and DNA (λmax 260 nm and extinction E=6.6×10$^3$) after treatment of 15 μg of the modified DNA with 5 mM dithiothreitol (Sigma Chemical Co.) for 1.5 h at 20° C.

The labeled DNA was treated with 20 mM dithiothreitol (DTT, Sigma Chemical Co.) for 1 hour at 4° C. to generate free thiols on the labeled plasmid. Reverse micelles were prepared by dissolving 82 μL of 1 μg/μL Cys-DNA in 2.2 mL $C_{12}E_4$/TMP (Wo=6.58). The mixtures were agitated using a vortex stirrer until a transparent solution was obtained (usually 2 min). After formation of the micelles, sodium periodate was added to a final concentration of 2 mM with respect to the total aqueous portion to oxidize the thiols to disulfides. The samples were centrifuged for 1 min at 14,000 rpm to remove any aggregates. A control reaction was prepared following the same procedure using non-labeled DNA. The samples were incubated at 4° C. for 2 hours. The reverse micelle system was disrupted with the addition of 55 μL ethanol, 275 μL of 20 mM MOPS pH 7.5, 0.1 mM EDTA buffer, and 1.1 mL ethyl acetate. The reaction was vortexed and separated into two layers via centrifugation. The aqueous layer was washed twice with 2 mL ethyl acetate and once with 3 mL diethyl ether. The samples were then analysed by agarose gel electrophoresis.

Results:

Agarose gel electrophoresis, indicated that periodate oxidized, cysteine DNA was found to remain in the well (indicating intramolecular oxidation of cysteine groups on the DNA). The non-oxidized cysteine DNA migrated into the gel similarly to the unmodified DNA control.

Example 14

Mouse Tail Vein Injections of Oxidized Cysteine-pDNA(pCI Luc) Complexes Formed in a Reverse Micelle Procedure:

PCILuc DNA (PDNA) (Zhang, G., Vargo, D., Budker, V., Armstrong, N., Knechtle, S., Wolff, J. A. Human Gene Therapy, 8, 1763–1772, 1997) was modified with Cysteine Label IT® at weight ratios of 0.1:1 and 0.2:1 (reagent:DNA) at 37° C. for 1 hour. The labeled DNA was treated with 20 mM dithiothreitol (DTT, Sigma Chemical Co.) for 1 hour at 4° C. to generate free thiols on the labeled plasmid. Reverse micelles were prepared as described in Example 13. For each weight ratio, both an oxidized (sodium periodate added to the reverse micelle) and a non-oxidized sample (no sodium periodate was added) were prepared. The pDNA was isolated as previously described.

Five complexes were prepared as follows:
Complex I: pDNA (pCI Luc, 30 μg) in 7.5 mL Ringers.
Complex II: 0.1:1 cysteine labeled pDNA (pCI Luc, 30 μg) non-oxidized, in 7.5 mL Ringers.
Complex III: 0.1:1 cysteine labeled pDNA (pCI Luc, 300 μg) oxidized in the reverse micelle,in 7.5 mL Ringers.
Complex IV: 0.2:1 cysteine labeled pDNA (pCI Luc, 30 μg) non-oxidized, in 7.5 mL Ringers.
Complex V: 0.2:1 cysteine labeled pDNA (pCI Luc, 30 μg) oxidized in the reverse micelle, in 7.5 mL Ringers.

Plasmid delivery in the tail vein of ICR mice (n=3) was performed as described. Tail vein injections of 2.5 mL of the complex were preformed using a 30 gauge, 0.5 inch needle.

One day after injection, the animal was sacrificed, and a luciferase assay was conducted on the liver. Luciferase expression was determined as previously reported (Wolff, J. A., Malone, R. W., Williams, P., Chong, W., Acsadi, G., Jani, A. and Felgner, P. L. Direct gene transfer into mouse muscle in vivo. Science, 1465–1468, 1990.). A Lumat LB 9507 (EG&G Berthold, Bad-Wildbad, Germany) luminometer was used.

Results: 2.5 mL injections
Complex I: 17,113,000 RLU
Complex II: 21,111,000 RLU
Complex III: 11,998,000 RLU
Complex IV: 2,498,000 RLU
Complex V: 4,498,000 RLU Results:

The luciferase assay indicates that the pDNA that is oxidized within the reverse micelle is functional and able to be expressed.

Experiment 15

Synthesis of β-D-Glucopyranosyl Decane Disulfide and O-Glycine-β-D-Glucopyranosyl Decane Disulfide Procedure:

To a solution of decane thiol (0.59 mL, 2.9 mmol, Aldrich Chemical Company) in 11 mL $CHCl_3$ was added sulfuryl chloride (0.46 mL, 5.7 mmol, Aldrich Chemical Company), and the resulting mixture was stirred at room temperature for 18 h. Removal of solvent (aspirator), afforded decansulfenyl chloride.

To a solution of decansulfenyl chloride (190 mg, 0.92 mmol) in 4 mL acetonitrile was added 1-thio-β-D-glucose sodium salt hydrate (200 mg, 0.92 mmol, Aldrich Chemical Company) and 15-crown-5 (0.18 mL, 0.899 mmol, Aldrich Chemical Company). The resulting mixture was stirred at ambient temperature for 16 h, filtered, and precipitated in Et$_2$O. The residue was triturated with Et$_2$O and purified by reverse phase HPLC on an Aquasil C18 column (Keystone Scientific Inc.), 10–90% B, 20 min (A=0.1% TFA in H$_2$O, B=0.1% TFA in Acetonitrile). Lyophilization afforded 10 mg (3%) of β-D-glucopyranosyl decane disulfide as a fine white solid.

To a solution of β-D-glucopyranosyl decane disulfide (8 mg, 0.02 mmol) in 80 μL THF was added N-Boc glycine (15 mg, 0.09 mmol, Sigma Chemical Company), DCC (18 mg, 0.09 mmol, Aldrich Chemical Company), and a catalytic amount of dimethylaminopyridine (Aldrich Chemical Company). The resulting solution was stirred at ambient temperature for 12 h, and centrifugated to remove the solid. The resulting solution was concentrated under reduced pressure, resuspended in dichloromethane, filtered through a plug of silica gel, and concentrated (aspirator). The Boc protecting group was removed by taking the residue up in 200 μL of 2.5% TIS/50% TFA/dichloromethane for 12 h. Removal of solvent (aspirator), followed by purification by reverse phase HPLC on a Aquasil C18 column (Keystone Scientific Inc.), 10–90% B, 20 min (A=0.1% TFA in H$_2$O, B=0.1% TFA in Acetonitrile) afforded 0.7 mg (5%) of O-glycine-β-D-glucopyranosyl decane disulfide as a fine white solid following lyophilization.

Example 16

Synthesis of β-D-Glucopyranosyl Cholesterol Disulfide

By similar methodology as described in example 15, β-D-glucopyranosyl cholesterol disulfide was isolated (12% yield).

Experiment 17

Synthesis of Two Tailed β-D-Glucopyranosyl Disulfide Derivatives

β-D-Glucopyranosyl N-Dodecanoyl-Cysteine-Dodecanoate Disulfide and O-Glycine-β-D-Glucopyranosyl N-Dodecanoyl-Cysteine-Dodecanoate Disulfide.

Procedure:

To a solution of N-FMOC-S-Trt-Cysteine (585 mg, 1.0 mmol, NovaBioChem) in 4 mL dichloromethane was added 1-dodecanol (240 mg, 1.3 mmol, Aldrich Chemical Company), DCC (260 mg, 1.3 mmol, Aldrich Chemical Company), and a catalytic amount of dimethylaminopyridine (Aldrich Chemical Company). The resulting solution was stirred at ambient temperature for 30 min, filtered, and purified by flash chromatography on silica gel (10–20% EtOAc/hexane eluent). Removal of solvent (aspirator) afforded 572 mg (76%) of the protected cysteine-dodecanoate.

To a solution of protected cysteine-dodecanoate (572 mg, 0.76 mmol) was added 3 mL of 20% piperidine in DMF. The resulting solution was stirred at ambient temperature for 1 h, and partitioned in EtOAc/H2O. The aqueous layer was extracted 2×EtOAc. The combined organic layer was washed 2×1N HCl, dried (Na2SO4), and concentrated to afford S-Trt-cysteine-dodecanoate. The residue was suspended in 2 mL dichloromethane, and cooled to −20° C. Diisopropylethylamine (0.16 mL, 0.92 mmol, Aldrich Chemical Company) was added followed dodecanoyl chloride (0.26 mL, 1.1 mmol, Aldrich Chemical Company), and the solution was allowed to slowly warm to ambient temperature. After 1 h, the solvent was removed (aspirator), and the residue partitioned in EtOAc/H2O. The organic layer was washed 2×1 N HCl, 1×brine, dried (Na2SO4), and the solvent was removed (aspirator). The resulting residue was suspended in 2% TIS/50% TFA/dichloromethane to remove the trityl protecting group. After 4 h the solution was concentrated, and the resulting residue was purified by flash column chromatography on silica gel (10–20% EtOAc/hexanes eluent) to afford 180 mg (42%) N-dodecanoyl-cysteine-dodecanoate (M+1=472.6).

To a solution of N-dodecanoyl-cysteine-dodecanoate (180 mg, 0.38 mmol) in 0.5 mL chloroform was added sulfuryl chloride (62 μL, 0.76 mmol, Aldrich Chemical Company). The resulting solution was stirred at ambient temperature for 2 h and the solvent was removed (aspirator). The resulting residue was suspended in 1 mL acetonitrile, and 1-thio-β-D-glucose sodium salt hydrate (85 mg, 0.39 mmol, Aldrich Chemical Company) and 15-crown-5 (76 μL, 0.38 mmol, Aldrich Chemical Company) were added. After 1 h at ambient temperature the solvent was removed (aspirator) and the residue was partitioned in EtOAc/H2O. The organic layer was concentrated and the resulting residue was purified by flash column chromatography on silica gel (5–10% MeOH/0.1% TFA/dichloromethane eluent) to afford 19 mg (8%) β-D-glucopyranosyl N-dodecanoyl-cysteine-dodecanoate disulfide.

To a solution of β-D-glucopyranosyl N-dodecanoyl-cysteine-dodecanoate disulfide (3.9 mg, 0.0045 mmol) in 100 μL dichloromethane was added N-Boc glycine (3.2 mg, 0.018 mmol, Sigma Chemical Company), DCC (3.8 mg, 0.018 mmol, Aldrich Chemical Company), and a catalytic amount of dimethylaminopyridine (Aldrich Chemical Company). The resulting solution was stirred at ambient temperature for 4 h, and filtered. The Boc protecting group was removed by taking the residue up in 2 mL of 1% TIS/50% TFA/dichloromethane for 2 h. Removal of solvent (aspirator), followed by purification by reverse phase HPLC on a Diphenyl column (Vydaq), 20–90% B, 20 min (A=0.1% TFA in H$_2$0, B=0.1% TFA in Acetonitrile) afforded 3.6 mg (90%) of O-glycine-β-D-glucopyranosyl decane disulfide as a fine white solid following lyophilization.

Experiment 18

Synthesis of Disulfide Containing Surfactants

1). Synthesis of the Disulfide of Decanethiol and 3-Dimethylamino-Thiopropionamide.

Procedure:

To a solution of thiopropionic acid (0.41 mL, 4.7 mmol, Aldrich Chemical Company) in 18 mL CH$_2$Cl$_2$ was added diisopropylethylamine (0.82 mL, 4.7 mmol, Aldrich Chemical Company) followed by trityl chloride (1.4 g, 4.9 mmol, Aldrich Chemical Company). The resulting mixture was stirred at room temperature for 18 h. Removal of solvent (aspirator) afforded a white crystalline solid. The material was partitioned in EtOAc/H$_2$O, and washed with 0.1 M NaHCO$_3$ and 1×brine. Concentrated to afford S-trityl thiopropionic acid.

To a solution of S-trityl-thiopropionic acid (0.30 g, 0.86 mmol) in 3.5 mL CH$_2$Cl$_2$ was added PyBOP (0.45 g, 0.86 mmol, NovaBioChem). The mixture was stirred at ambient temperature for 5 min and then dimethylaminopropylamine (0.11 mL, 0.86 mmol, Aldrich Chemical Company) was added. The solution was stirred at room temperature for 18 h, and concentrated. The residue was brought up in EtOAc and partitioned in H$_2$O. The organic layer was washed 2×H$_2$O, 1×brine, dried (Na$_2$SO$_4$), and the solvent removed (aspirator). The resulting residue was suspended in 2% TIS/50% TFA/CH$_2$Cl$_2$ (3 mL) to remove the trityl protecting group. After 2 h the solution was concentrated to afford 3-dimethylamino-thiopropionamide.

To a solution of 3-dimethylamino-thiopropionamide (0.082 g, 0.43 mmol) in 1.5 mL dichloromethane was added decanethiolchloride (0.090 g, 0.43 mmol, prepared as in example 15). The resulting solution was stirred at ambient temperature for 20 min. The solvent was removed and the resulting residue was purified by flash column chromatography on silica gel (15% MeOH/CH$_2$Cl$_2$ eluent) to afford 17.2 mg (9%) of the disulfide of decanethiol and 3-dimethylamino-thiopropionamide (M+1=363.4).

2). Synthesis of the Disulfide of Dodecanethiol and 3-Dimethylamino-Thiopropionamide.

Procedure:

By a similar procedure as above, thiopropyl-dimethylaminopropylamine (0.10 g, 0.52 mmol) in 2.0 mL dichloromethane was added dodecanethiolchloride (0.12 g, 0.52 mmol). The resulting solution was stirred at ambient temperature for 20 min. The solvent was removed and a portion of the resulting residue (160 mg) was purified by flash column chromatography on silica gel (10% MeOH/CH$_2$Cl$_2$ eluent) to afford 22.4 mg (14%) of the disulfide of dodecanethiol and 3-dimethylamino-thiopropionamide (M+1=391.4).

3). Synthesis of the Disulfide of Decanethiol and Thiopopionic-3-Dimethylaminopropanoate.

Procedure:

To a solution of trityl-S-thiopropionic acid (0.36 g, 1.0 mmol) in 4.0 mL CH$_2$Cl$_2$ was added PyBOP (0.54 g, 1.0 mmol, NovaBioChem). The mixture was stirred at ambient temperature for 5 min before the addition of dimethylaminopropanol (0.12 mL, 1.0 mmol, Aldrich Chemical Company). The solution was stirred at room temperature for 18 h, and concentrated. The residue was brought up in EtOAc and partitioned in H$_2$O. The organic layer was washed 2×H$_2$O, 1×brine, dried (Na$_2$SO$_4$), and the solvent removed (aspirator). The resulting residue was suspended in 2% TIS/50% TFA/CH$_2$Cl$_2$ (3 mL) to remove the trityl protecting group. After 2 h the solution was concentrated to afford thiopopionic-3-dimethylaminopropanoate.

To a solution of thiopopionic-3-dimethylaminopropanoate (0.10 g, 0.52 mmol) in 2 mL dichloromethane was added decanethiolchloride (0.11 g, 0.52 mmol). The resulting solution was stirred at ambient temperature for 20 min. The solvent was removed and a portion of the resulting residue (25 mg) was purified by plug filtration on silica gel (10% MeOH/CH$_2$Cl$_2$ eluent) to afford 20.9 mg (84%) of the disulfide of decanethiol and thiopopionic-3-dimethylaminopropanoate (M+1=364.4).

4). Synthesis of the Disulfide of Dodecanethiol and Thiopopionic-3-Dimethylaminopropanoate.

Procedure:
To a solution of thiopopionic-3-dimethylaminopropanoate (0.10 g, 0.52 mmol) in 2 mL dichloromethane was added dodecanethiolchloride (0.11 g, 0.52 mmol). The resulting solution was stirred at ambient temperature for 20 min. The solvent was removed and a portion of the resulting residue (150 mg) was purified by flash column chromatography on silica gel (1% TFA/10% MeOH/$CH_2Cl_2$ eluent) to afford 38 mg (25%) of the disulfide of decanethiol and thiopopionic-3-dimethylaminopropanoate (M+1=392.4).

Experiment 19

Synthesis of Silicone Containing Amphipathic Molecules

1. Synthesis of 3-dimethylamino-dimethyloctadecyl silyl ether.

To a solution of 3-dimethylamino-1-propanol (0.873 mmol, Aldrich Chemical Company) in 2 mL chloroform was added dimethyloctadecyl chlorosilane (378 mg, 1.09 mmol, Aldrich Chemical Company) and imidazole (74.2 mg, 1.09 mmol, Aldrich Chemical Company). After 16 hrs at ambient temperature, the solution was partitioned in EtOAc/H2O with 10% sodium bicarbinate. The organic layer was washed with water, and brine. The solvent was removed (aspirator) to afford 328 mg (91%) of 3-dimethylamino-dimethyloctadecyl silyl ether as a cream colored solid.

2. Synthesis of 3-(dimethylamino)-1,2-dimethyloctadecyl silyl ether.

To a solution of 3-(dimethylamino)-1,2-propanediol (50.0 mg, 0.419 mmol, Aldrich Chemical Company) in 2 mL chloroform was added dimethyloctadecyl chlorosilane (328 mg, 0.944 mmol, Aldrich Chemical Company) and imidazole (68.1 mg, 0.944 mmol, Aldrich Chemical Company). After 16 hrs at ambient temperature, the solution was partitioned in EtOAc/H2O with 10% sodium bicarbinate. The organic layer was washed with water, and brine. The solvent was removed (aspirator) to afford 266 mg (86%) of 3-(dimethylamino)-1,2-dimethyloctadecyl silyl ether as a white solid.

Experiment 20

Application of Reverse Micellar Formulations to Mouse Dermis

Procedure:
Five Complexes were prepared:
Complex I. Doxorubicine hydrochloride was dissolved in water to a final concentration of 5.8 mg/mL. To a solution of 12 μL Brij 30 (Sigma Chemical Company) in 88 μL of tetramethylpentane was added 5 μL of the doxorubicine hydrochloride solution. The sample was vortexed for 2 min resulting in a clear red solution.

Complex II Doxorubicine hydrochloride was dissolved in water to a final concentration of 50 mg/mL. To a solution of 10 μL of Brij 30 (Sigma Chemical Company) and 2 mg β-D-glucopyranosyl decane disulfide in 190 μL of tetramethylpentane was added 5 μL of the doxorubicine hydrochloride solution. The sample was vortexed for 2 min resulting in a clear red solution.

Complex III Doxorubicine hydrochloride was dissolved in water to a final concentration of 50 mg/mL. To a solution of 10 μL of Brij 30 (Sigma Chemical Company) and 0.5 mg O-Glycine-β-D-glucopyranosyl decane disulfide in 190 μL of tetramethylpentane was added 5 μL of the doxorubicine hydrochloride solution. The sample was vortexed for 2 min resulting in a clear red solution.

Complex IV Doxorubicine hydrochloride was dissolved in water to a final concentration of 50 mg/mL. To a solution of 10 μL of Brij 30 (Sigma Chemical Company) and 6 mg 3-dimethylamino-dimethyloctadecyl silyl ether in 190 μL of tetramethylpentane was added 5 μL of the doxorubicine hydrochloride solution. The sample was vortexed for 2 min resulting in a clear red solution.

Complex V Doxorubicine hydrochloride was dissolved in water to a final concentration of 50 mg/mL. To 200 μL H2O was added 5 μL of the doxorubicine hydrochloride solution.

ICR mice were anesthetize, and the hair removed from the back of the neck, and on one animal the abdominal skin. After 1 h the animals were sacrificed, and the skin samples removed and examined. The complexes were applied to the dermis as follows:

Complex I. The complex was applied by immersing a cotton swab in the solution, and swabbing the abdominal skin and the dehaired skin on the back of the neck.

Complex II–V. The complex was applied by dropping 50 μL of solution onto the back of the neck.

Results:
Fluorescent examination of the skin samples (O.C.T. frozen, UV light). Samples from the application of Complex I were showed a much lower level of positive cells than from Complexes II–IV.

| Complex | Number | Location of the label |
|---|---|---|
| I | Abdominal skin | Positive label is restricted to nuclei only with majority of them being epithelium cells. Small portion of positive sells are connective tissue cells adjoining to the labeled epithelium cells. |
|  | Skin from the back | Similar pattern of labeling. |
| II | 7477 | Whole epithelium compartment is very bright, not specifically nuclei. Some connective tissue cells in deeper part of derma are positive. No positive follicular cells. |
|  | 7479 | Whole epithelium compartment is very bright, not specifically nuclei. Some connective tissue |

-continued

| Complex | Number | Location of the label |
|---|---|---|
| | | cells in deeper part of derma are positive. Very rare positive follicular cells. |
| III | 6939 | Whole epithelium compartment is very bright, not specifically nuclei. Some follicular cells are positive. |
| | 7459 | Whole epithelium compartment is very bright, not specifically nuclei. Some follicular cells are positive |
| IV | 7476 | Whole epithelium compartment is positive but less than in previous two groups, some connective tissue cells in deeper part of derma are positive. |
| | 7460 | Whole epithelium compartment is positive, some connective tissue cells in deeper part of derma are positive. |
| V | 7474 | Mostly only the skin surface is positive, occasionally some deeper cells, probably damaged areas (shaving) Cells and nuclei are negative. |
| | 7463 | Mostly only the skin surface is positive, occasionally. Cells and nuclei are negative. |
| Water | | Negative |

Analysis:

Reverse micelles are able to incorporate doxorubicine hydrochloride and deliver the drug to the epithelium.

New Definitions to include in the specification:

A reactive functional group means a bond that can undergo chemical modification or reaction.

The term cargo means pharmaceuticals, proteins, peptides, hormones, cytokines, antigens and small molecules.

Substructure means the chemical structure of the compound and any compounds derived from that chemical structure from the replacement of one or more hydrogen atoms by any other atom or change in oxidation state. For example if the substructure is succinic anhydride, then methylsuccinic anhydride, 2,2-dimethylsuccinic anhydride, 3-oxabicyclo[3.1.0]hexane-2,4-dione, maleic anhydride, citriconic anhydride, and 2,3-dimethylmaleic anhydride have the same substructure.

The foregoing examples are considered as illustrative only of the principles of the invention. Further, since numerous modifications and changes will readily occur to those skilled in the art, it is not desired to limit the invention to the exact construction and operation shown and described. Therefore, all suitable modifications and equivalents fall within the scope of the invention.

We claim:

1. A process for delivering a nucleic acid to a cell, comprising:
    a) inserting the nucleic acid into a reverse micelle, wherein the reverse micelle comprises a plurality of neutral, negative, or zwitterionic amphipathic molecules containing reactive functional groups;
    b) polymerizing two or more of the amphipathic molecules thereby forming a polymerized reverse micelle; and,
    c) contacting the cell with the polymerized reverse micelle.

2. The process of claim 1 wherein at least one of the amphipathic molecules contains a labile bond.

3. The process of claim 2 wherein cleavage of the labile bond disrupts the reverse micelle.

4. The process of claim 2 wherein the labile bond consists of a disulfide bond.

5. The process of claim 2 wherein the labile bond consists of a silicon-heteroatom bond.

6. The process of claim 2 wherein the labile bond consists of an amide constructed from a compound having a substructure of succinic anhydride.

7. A reverse micelle containing a nucleic acid formed by the process comprising:
    a) inserting the nucleic acid into a negatively-charged, zwitterionic, or neutral reverse micelle, wherein the reverse micelle comprises a plurality of amphipathic compounds containing reactive functional groups capable of participating in a polymerization reaction; and
    b) polymerizing two or more of the amphipathic compounds.

8. The complex of claim 7 wherein at least one of the amphipathic molecules contains a biologically labile bond.

9. The complex of claim 8 wherein cleaving the biologically labile bond disrupts the reverse micelle.

10. The complex of claim 7 wherein the nucleic acid is compacted.

* * * * *